(12) United States Patent
Phan et al.

(10) Patent No.: US 9,775,527 B2
(45) Date of Patent: Oct. 3, 2017

(54) METHOD AND APPARATUS FOR SIMULATION OF PRESSURE TRANSDUCER FOR MEASUREMENT OF BLOOD PRESSURE

(71) Applicant: Edwards Lifesciences Corporation, Irvine, CA (US)

(72) Inventors: Luong N. Phan, San Clemente, CA (US); Feras Al Hatib, Irvine, CA (US); Mark A. Konno, Laguna Beach, CA (US); Lindon A. Baker, Yorba Linda, CA (US); Richard A. Gros, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 156 days.

(21) Appl. No.: 14/710,329

(22) Filed: May 12, 2015

(65) Prior Publication Data
US 2016/0324428 A1    Nov. 10, 2016

Related U.S. Application Data

(63) Continuation of application No. PCT/US2013/054558, filed on Aug. 12, 2013.

(60) Provisional application No. 61/695,742, filed on Aug. 31, 2012.

(51) Int. Cl.
*A61B 5/00* (2006.01)
*A61B 5/021* (2006.01)

(52) U.S. Cl.
CPC ........ *A61B 5/02141* (2013.01); *A61B 5/0002* (2013.01); *A61B 5/021* (2013.01); *A61B 5/7278* (2013.01); *A61B 2560/0223* (2013.01); *A61B 2560/045* (2013.01)

(58) Field of Classification Search
CPC .................................................. A16B 5/02141
See application file for complete search history.

(56) References Cited

U.S. PATENT DOCUMENTS

| | | |
|---|---|---|
| 3,868,679 A | 2/1975 | Arneson |
| 2003/0045781 A1 | 3/2003 | Rosenheimer |
| 2012/0071744 A1 | 3/2012 | Euliano, II et al. |

(Continued)

OTHER PUBLICATIONS

Int'l. Search Report, Dec. 17, 2013.

*Primary Examiner* — Clayton E Laballe
*Assistant Examiner* — Dennis Hancock
(74) *Attorney, Agent, or Firm* — Blakely, Sokoloff, Taylor & Zafman LLP; Eric T. King

(57) ABSTRACT

Disclosed is an apparatus, system, and method for utilizing a pressure transducer simulator that is configured for use with a pressure sensor device and a patient monitoring device. The pressure transducer simulator may be configured to generate a simulation of the output of an analog pressure sensing device to be compatible with the patient monitoring device. The simulation may be based upon a pressure signal received from the pressure sensor device. In one embodiment, the pressure transducer simulator includes a digital potentiometer that is configured to generate an analog signal based upon the pressure signal received from the pressure sensor device and wherein the digital potentiometer is configured to transmit the analog signal to the patient monitoring device.

17 Claims, 3 Drawing Sheets

(56) References Cited

U.S. PATENT DOCUMENTS

2012/0316794 A1 12/2012 Goh et al.
2014/0182352 A1* 7/2014 Hersh ................ A61B 5/02141
　　　　　　　　　　　　　　　　　　　　　73/1.57

* cited by examiner

METHOD AND APPARATUS FOR SIMULATION OF PRESSURE TRANSDUCER FOR MEASUREMENT OF BLOOD PRESSURE

BACKGROUND

Field

The present invention relates to a pressure transducer simulator that is configured for use with a pressure sensor device and a patient monitoring device. The pressure transducer simulator may be configured to generate a simulation of the output of an analog pressure sensing device to be compatible with the patient monitoring device.

Relevant Background

A standard analog pressure device for measuring blood pressure (typically known as a Disposable Pressure Transducer or DPT) includes a pressure transducer, which is basically a bridge circuit in which a reference signal is applied to one branch of the bridge and the pressure signal is obtained on the other branch. The pressure sensing element (typically a piezoelectric sensor) is placed in one, two, three or four of the four arms of the bridge. The pressure sensing element is basically a variable resistance that varies with the applied pressure. The analog pressure sensing device is usually connected through a fluid filled system to a catheter placed in a vein or an artery, where the pressure pulsations are captured by the pressure sensing element. The analog pressure sensing device is typically for blood pressure monitoring.

The other side of the analog pressure sensing device is typically connected to a measurement instrument, typically a bedside monitor, a blood pressure monitor, or any other monitor that uses the blood pressure signal (e.g., pulse contour Cardiac Output monitors). A reference signal to the analog pressure sensing device is typically provided by the measurement instrument and it is typically used by the instrument to scale the measured blood pressure signal. Different monitors have different reference signals. The reference signal may be either DC or AC and may be typically in the 1-10 Volt range. In AC-based instruments, the operating frequency typically ranges from a few kHz up to 5 kHz.

Unfortunately, standard monitors are generally configured to only interact with particular types of analog pressure sensing devices (e.g., blood pressure devices) and cannot interact with waveforms from other types of pressure sensing devices, such as digital non-invasive blood pressure monitors (NIBMs).

SUMMARY

Embodiments of the invention may relate to an apparatus, system, and method for utilizing a pressure transducer simulator that is configured for use with a pressure sensor device and a patient monitoring device. The pressure transducer simulator may be configured to generate a simulation of the output of an analog pressure sensing device to be compatible with the patient monitoring device. The simulation may be based upon a pressure signal received from the pressure sensor device. In one embodiment, a pressure transducer simulator includes a digital potentiometer that is configured to generate an analog signal based upon the pressure signal received from the pressure sensor device and wherein the digital potentiometer is configured to transmit the analog signal to the patient monitoring device.

DETAILED DESCRIPTION

Embodiments of the invention generally relate to an apparatus, system, and method to simulate the function of a standard analog pressure sensor. In particular, an apparatus, system, and method is provided that allows for broad and universal connectivity to existing pressure monitoring devices, regardless of the type of reference signal (AC or DC) and/or the amplitude of the reference signal, and regardless of the type of input signal (e.g., analog or digital). Embodiments of the invention have many practical applications.

In particular, embodiments of the invention provide an easy and universal connectivity to all types of blood pressure measuring monitors. This capability of universal connectivity makes it possible to connect various continuous noninvasive blood pressure monitors (NIBMs) (i.e., blood pressure sensing devices) to already existing and clinically adopted blood pressure measuring monitors, which are currently used for invasive measurements only (i.e., from analog blood pressure sensing devices, or disposable pressure transducers—DPTs).

Many new technologies for noninvasive continuous measurement of blood pressure (i.e., digital pressure sensor devices) are available today. The possibility of connecting those various technologies to standard patient monitoring devices is an easy and low cost way to provide noninvasive measurements in the clinical setting. Embodiments of the invention allow for the noninvasive pressure signal to be directly acquired through the regular pressure transducer connector with no need to develop special modules for the different blood pressure measuring devices or patient monitors. This allows the display of the noninvasive pressure measurements (i.e., measurements from noninvasive pressure sensor devices) on the patient monitoring device in the exact same way as the currently used invasive pressure measurements (i.e., analog measurements from analog pressure sensor devices, or DPTs).

Embodiments of the invention to achieve this functionality will be hereinafter described. It should be noted that although digital pressure sensor devices and analog pressure sensor devices in conjunction with a patient monitoring device have been previously described for use with blood pressure measurements that embodiments of the invention may relate to the pressure measurements of many different types of patient measurements (e.g., cardiac measurements, breathing measurements, intracranial pressure measurements etc.)

Figure 1:
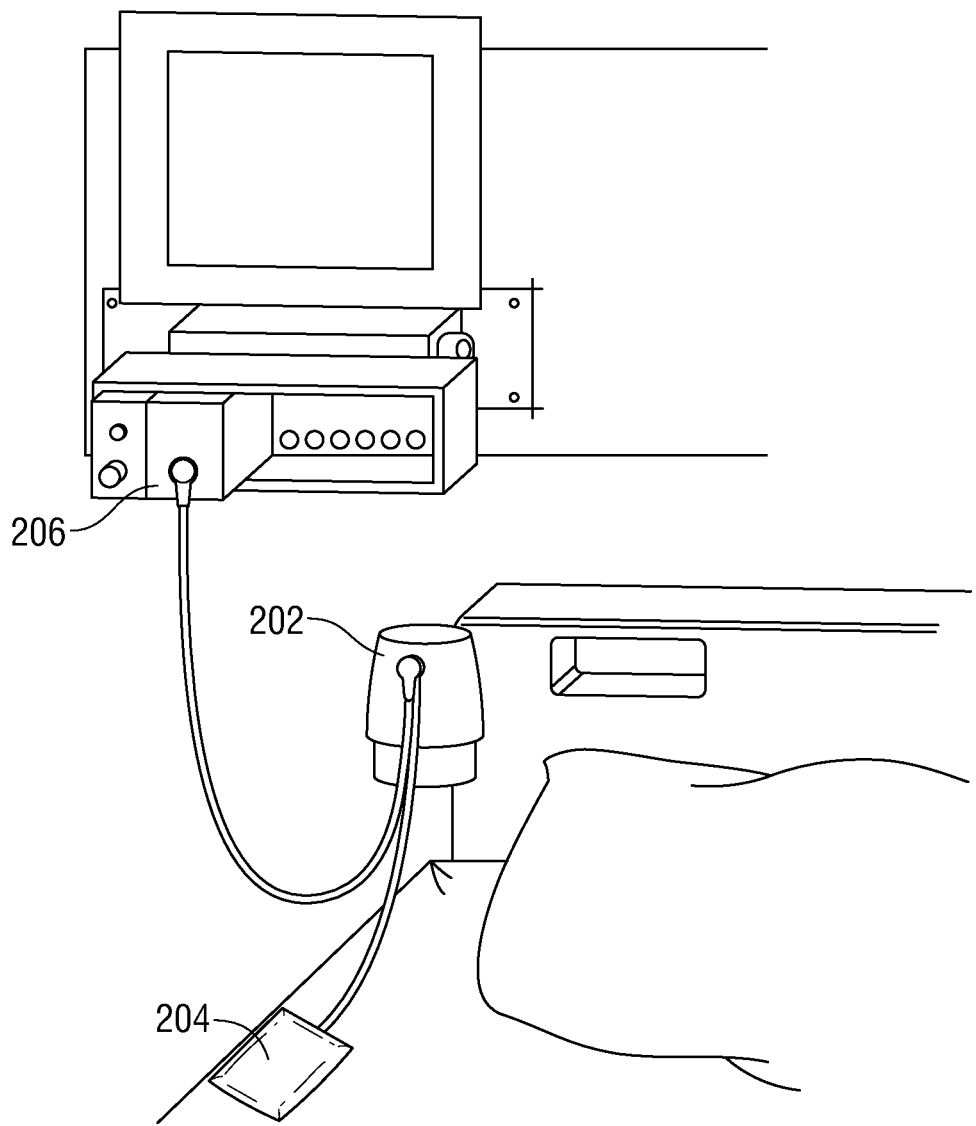
FIG. 1 is a diagram of a system in which embodiments of the invention related to a pressure transducer simulator may be practiced.
Figure 2:
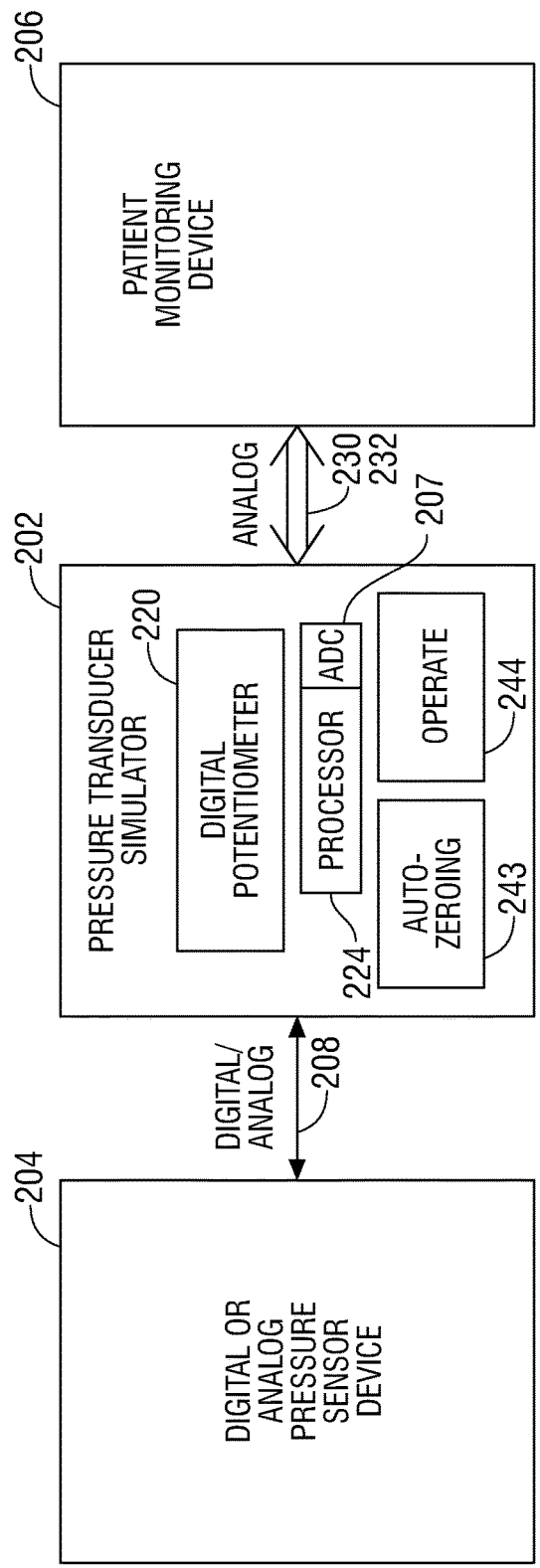
FIG. 2 is a block diagram illustrating components of the pressure transducer simulator, according to one embodiment of the invention.

In order to achieve this functionality, with reference to FIGS. 1 and 2, in one embodiment, a pressure transducer simulator integrated into a noninvasive blood pressure measuring instrument 202 may be configured for use with an invasive or noninvasive blood pressure module 204 and a patient monitoring device 206. The patient monitoring device 206 may include a display screen to show a patient's blood pressure reading. The pressure transducer simulator integrated in the noninvasive blood pressure measuring instrument 202 may be directly connected to a pre-existing connector of the invasive blood pressure module of the patient monitoring device 206.

The pressure transducer simulator in measuring instrument 202 may be configured to generate a simulation of the output of an analog pressure sensing device compatible with the monitoring device 206, wherein the simulation is based upon a pressure signal 208 received from the pressure sensor device 204. The pressure transducer simulator in 202 may comprise a digital potentiometer 220 and a processor 224, as well as other components to be hereinafter described. The pressure transducer simulator in measuring instrument 202 will hereinafter be referred to as pressure transducer simulator 202.

In one embodiment, the pressure transducer simulator 202 may include a digital potentiometer 220 that is configured to generate an analog signal 230/232 that is transmitted to the patient monitoring device 206 for display on the patient monitoring device 206. It should be noted that the connections of digital or analog signals between a patient (not shown) to digital or analog pressure sensor devices 204, to pressure transducer simulator 202, to patient monitoring device 206, etc., may be through wired or wireless connections. Further, as will be described, the pressure transducer simulator 202 may be utilized with either digital or analog pressure sensing devices 204 that transmit digital or analog pressure signals 208. Also, it should be appreciated that pressure sensing device 204 may relate to the pressure measurements of many different types of patient measurements (e.g., blood pressure measurements, cardiac measurements, breathing measurements, intracranial pressure measurements etc.) and may communicate in a wired or wireless manner and may be connected to different patient body parts (e.g., finger, ear, nose, arm, etc.). Any type of commonly utilized pressure sensing device 204 may be utilized with embodiments of invention utilizing the pressure transducer simulator.

Figure 3:
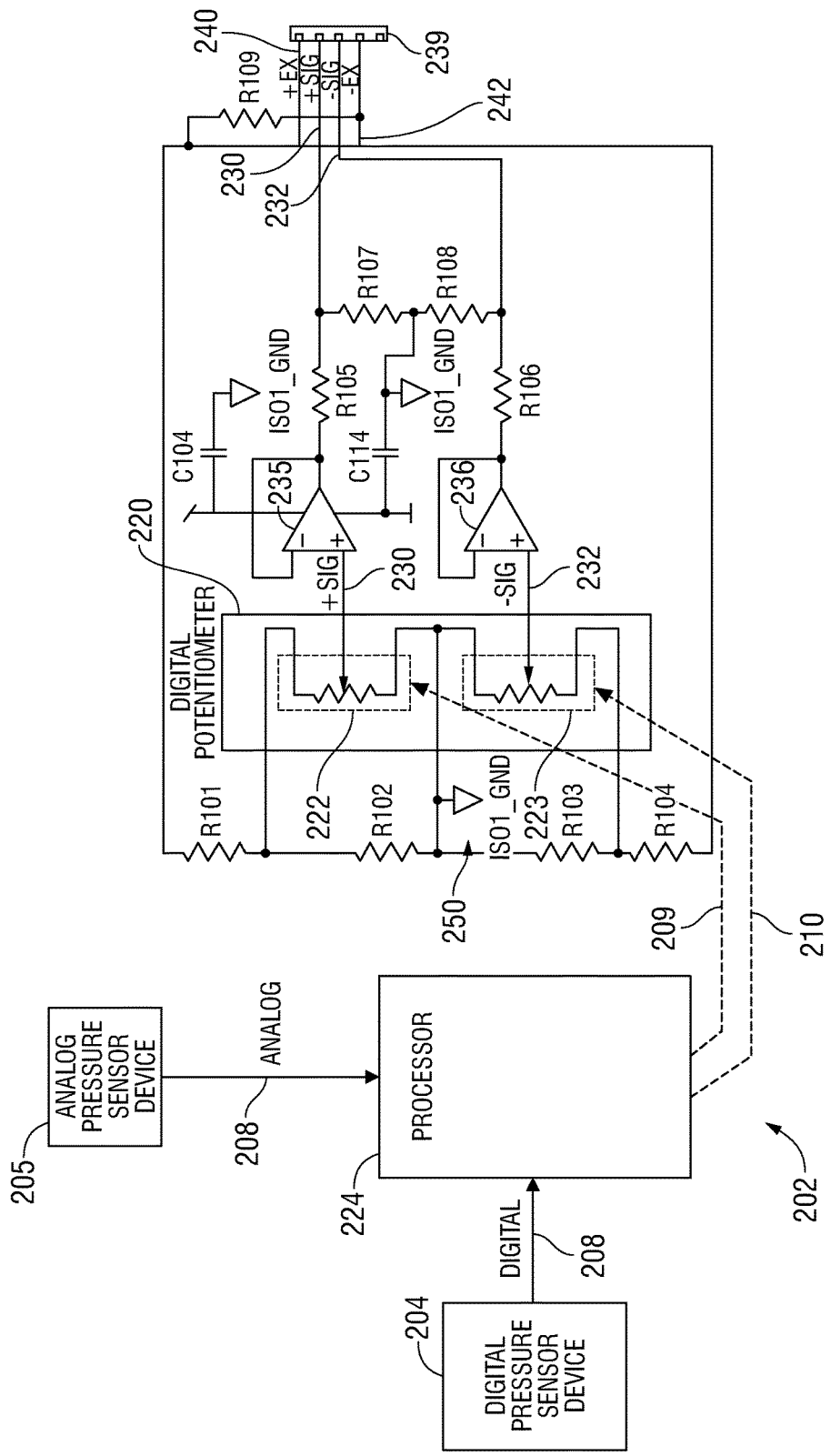
FIG. 3 is a diagram illustrating examples of circuit components of the pressure transducer simulator, according to one embodiment of the invention.

With additional reference to FIG. 3, digital potentiometer 220 may include first and second adjustable wipers 222 and 223. The first and second adjustable wipers 222 and 223 are adjustable to select the resistances of the first and second adjustable wipers 222 and 223. In this way, the analog output voltage signals (+SIG and −SIG) 230 and 232 may be selected and transmitted to the patient monitoring device 206. It should be noted that a connector 239 may connect the circuitry of the pressure transducer simulator 202 to the patient monitoring device 206. This may be to a pre-existing connector of the patient monitoring device 206. In this way, the pressure transducer simulator 202 is directly attachable to existing patient monitoring devices 206 and can provide signal inputs from either digital pressure sensor devices 204 or analog pressure sensor devices 205, as will be described. It should be noted that only one digital pressure sensor device 204 or one analog pressure sensor device 205 may be attached at a given time.

As is known to those of skill in the art, a digital potentiometer may be a digitally controlled electronic component that mimics the analog functions of a potentiometer. In particular, the resistance of the wipers may be digitally controlled such that a desired voltage is outputted.

In one embodiment, processor 224 may determine digital wiper settings for the adjustable wipers 222 and 223 to select the resistances of the digital wipers 222 and 223 and the analog output voltages (+SIG and −SIG) 230 and 232 of the digital potentiometer 200. Processor 224 may transmit digital wiper settings 209 and 210 to each of the adjustable wipers 222 and 223 to set their analog output voltages (+SIG and −SIG) 230 and 232.

In one embodiment, processor 224 of the pressure transducer simulator 202 may implement an auto-zeroing command. For example, an auto-zeroing button 243 may be configured for pressing by a medical technician to implement the auto-zeroing command. When the auto-zeroing command is implemented, each of the adjustable wipers 222 and 223 may be adjusted by digital wiper settings 209 and 210 selected by processor 224 and transmitted to the adjustable wipers 222 and 223 to set the resistances of the adjustable wipers 222 and 223 such that the analog signal produced by the digital potentiometer 220 and transmitted to the monitoring device 206 is approximately zero.

As an example, the resistances of the adjustable wipers 222 and 223 are controlled by processor 224 to set the resistances of the digital potentiometer 220 such that the analog signals (+SIG and −SIG) 230 and 232 produced by the digital potentiometer 220 are equal to one another such that they subtract each other out and are approximately zero. As one particular example, digital wiper settings 209 and 210 may be selected by processor 224 and transmitted to the adjustable wipers 222 and 223 to set the resistances of the adjustable wipers 222 and 223 to .5, then the analog signal produced by each of the adjustable wipers 222 and 223 of the digital potentiometer 220 would be .5*+SIG and .5*−SIG, respectively, such that (.5*+SIG)−(.5*−SIG) transmitted to the patient monitoring device 206 results in an approximately zero signal input. Based upon the auto-zeroing function, the patient monitoring device 206 can calibrate itself to the pressure transducer simulator 202.

Processor 224 may also implement an operate command. For example, an operate button 244 configured for pressing may be pressed by a medical technician and the operate command implemented. After implementation of the operate command, the digital potentiometer 220 produces analog signals (+SIG and −SIG) 230 and 232 based upon digital signals 208 from the digital pressure sensor device 204 and the digital wiper settings 209 and 210 selected by the processor 224. The analog signals (+SIG and −SIG) 230 and 232 are transmitted to the patient monitoring device 206. It should be appreciated that the use of an auto-zeroing button 243 and an operate button 244 to implement auto-zeroing commands and operate commands by processor 224 are merely examples, and that processor 224 may implement these commands automatically without the use of input commands from buttons or other input mechanisms. Further, a wide variety of different types of command input mechanisms at the pressure transducer simulator or at other locations may be utilized.

In particular, processor 224 may determine digital wiper settings 209 and 210 for the adjustable wipers 222 and 223 to select the resistances of the digital wipers 222 and 223 and the analog output voltages (+SIG and −SIG) 230 and 232 of the digital potentiometer 200. Processor 224 may transmit digital wiper settings 209 and 210 to each of the adjustable wipers 222 and 223 to select the analog output voltages (+SIG and −SIG) 230 and 232. In this way, processor 224 can ensure that analog output voltages (+SIG and −SIG) 230 and 232 match or are approximately equivalent to the digital pressure signal 208 from the digital pressure sensor device 204.

The previously-described pressure transducer simulator 202 of FIG. 3 accepts the DC or AC excitation voltage typically applied to an industry standard bridge type disposable pressure transducer (DPT) and outputs a standard differential signal of 5 µV per mmHg per volt of excitation. The pressure transducer simulator 202 accepts any excitation voltage within the range of −10 volts to +10 volts at pin 1 of connector 239 (signal name +EX) referenced to the excitation reference at pin 4 connector 239 (signal name −EX). The excitation can be constant or varying.

The digital potentiometer 220 is applied in a potentiometer voltage divider mode, analogous to a mechanical potentiometer. Digital potentiometer 220 performs an electronic adjustment function, similar to a mechanical potentiometer, but with enhanced resolution, solid state reliability, and strong temperature coefficient performance. In particular, as previously described, the desired wiper position of the adjustable wipers 222 and 223 for varying the resistance of the resistors is commanded digitally by processor 224.

The pressure transducer simulator 202 is universally compatible with a myriad of commercially available patient monitoring devices 206, because the differential output signals between +SIG and −SIG 230 and 232 are ratiometric to the instantaneous applied excitation voltage at 5 µV per mmHg per volt of excitation, and the differential output signals 230 and 232 ride on a common mode level tracking 50% of the instantaneous applied excitation voltage. Furthermore the output differential resistance of the pressure transducer simulator circuit, which is determined by resistors R107 and R108 is equivalent to the actual, differential resistance of the standard DPTs (the measurement arms of the bridge). Additionally, the resistance of the excitation path, which is determined by resistors R101, R102, R103, R104 and the resistances 222 and 223 of the digital potentiometer 220 is equivalent to the excitation resistance of the standard DPTs (the excitation arms of the bridge).

Resistor divider R101, R102, R103, and R104 scales the applied excitation voltage (+EX 240 and −EX 242) down based on the desired full scale differential output voltage. Advantageously, the circuit "ground" reference point (ISO1_GND 250) is at the midpoint of the applied excitation voltage. This will also be the midpoint, or common mode level, of the differential output signal. Thus, from the circuit perspective, the common mode voltage is zero, or ground, reducing circuit complexity.

As previously described, the pressure to be represented at the output is set by adjusting the adjustable wiper positions 222 and 223 of the digital potentiometer 220 under the control of processor 224. Because of the known excitation voltage of 5 µV per mmHg per volt of excitation utilized for patient monitoring devices and the known parameters of the wipers of the digital potentiometer 220, processor 224 implements a scaling function based upon the pressure signal 208 from the digital pressure sensor device 204 to select the wiper positions 222 and 223 of the digital potentiometer 220 to ensure that analog output voltages (+SIG and −SIG) 230 and 232 match or are approximately equivalent to the digital pressure signal 208 from the digital pressure sensor device 204. To provide an example, assuming a digital input 208 from digital pressure sensor device 204 of 100 mmHg or 1V, processor 224 would determine and transmit digital wiper settings 209 and 210 to the adjustable wipers 222 and 223 to select the resistances of the digital wipers 222 and 223 such that the analog output voltages (+SIG and −SIG) 230 and 232 of the digital potentiometer match and are approximately equivalent to the digital input. As an example, +SIG 230 may be set to 300 mmHg or 3V and −SIG 232 may be set to 200 mmHg or 2V such that these values are received by the patient monitoring device 206. In this example, the ultimate value would be (+SIG-(−SIG)) which is 100 mmHg or 1V that is equivalent to the digital input 208 from digital pressure sensor device 204. In this way, processor 224 can ensure that analog output voltages (+SIG and −SIG) 230 and 232 result in a match to the digital pressure input 208 from the digital pressure sensor device 204.

Further, as previously described, the pressure simulator transducer 202, in the same way, operates with analog pressure sensor devices. For example, analog pressure sensor device 205 may output a 100 mmHg or 1V analog input signal 208. Analog to digital converter (ADC) 207 may convert this to a digital input signal for use by processor 224, as previously described. It should be noted that ADC 207 may be a part of processor 224 or may be a separate component of the pressure transducer simulator 202 connected to processor 224. In the same way, processor 224 would determine and transmit digital wiper settings 209 and 210 to the adjustable wipers 222 and 223 to select the resistances of the digital wipers 222 and 223 such that the analog output voltages (+SIG and −SIG) 230 and 232 of the digital potentiometer match and are approximately equivalent to the digital input. As an example, +SIG 230 may be set to 300 mmHg or 3V and −SIG 232 may be set to 200 mmHg or 2V such that these values are received by the patient monitoring device 206. In this example, the ultimate value would be (+SIG-(−SIG)) which is 100 mmHg or 1V that is equivalent to the initial analog input from the analog pressure device 205. In this way, processor 204 can ensure that analog output voltages (+SIG and −SIG) 230 and 232 result in a match to the analog pressure input 208 from the analog pressure device 205.

Further, buffers 235 and 236 may be coupled to the digital potentiometer 220 to provide unity gain buffering for the adjustable wipers 222 and 223. It should be appreciated by those of skill in the art that because the digital potentiometer 220 is capable of only limited current and may have relatively high and non-constant source impedance, that the voltages at the wipers 222 may be unity gain buffered by buffers 235 and 236. Those skilled in the art will understand that the buffers 235 and 236 may have some offset voltage. Excessive offset voltage could result in unacceptable zero offset at the differential output, potentially resulting in rejection by some patient monitoring devices 206 such that resistor dividers R105, R107 and R106, R108 may be used to reduce the zero offset of the buffers 235 and 236 by a factor of approximately 13, ensuring low zero offset at the output. The R107 and R108 components of the dividers also provide a 300 ohm resistive path between +SIG and −SIG to satisfy a detection requirement of some commercially available pressure monitoring instruments. Moreover, in this previously described implementation, the desired output may be 5 µV per mmHg per volt of excitation, with 300 mmHg as full scale, so the full scale differential output is 1500 µV per volt of excitation, and the ratio of R101 to R102 is established taking into account the R105, R107 divider. Persons of ordinary skill in the art will recognize that other divider ratios could be used at R101 and R102 to accommodate other full scale ranges, or other ratios at R105, R107.

Additionally, the pressure transducer simulator 202 circuit may contain an additional feature to assist with presence detection by industry standard pressure monitoring instruments. R109 may present a current load on the excitation output (+EX 240) of the pressure monitoring instrument which is needed by some instruments to ensure detection.

Thus, embodiments of the invention relate to a pressure transducer simulator 202 that allows for broad and universal connectivity of a patient monitoring device 206 to both digital pressure sensor devices 204 and analog pressure sensor devices 205, regardless of the excitation voltages of patient monitoring device and/or the type of input signals (e.g., analog or digital) from either digital or analog pressure sensor devices.

In particular, embodiments of the invention provide an easy and universal connectivity to all types of blood pressure measuring monitors. This capability of universal connectivity makes it possible to connect various continuous noninvasive blood pressure monitors (NIBMs) (i.e., blood pressure sensing devices) to already existing and clinically adopted blood pressure measuring monitors, which are currently used for invasive measurements only (i.e., from analog blood pressure sensing devices, or disposable pressure sensors—DPTs). Embodiments of the invention allow for the noninvasive pressure signal to be directly acquired through the regular pressure transducer connector with no need to develop special modules for the different blood pressure measuring devices or patient monitors. This allows the display of the noninvasive pressure measurements (i.e., measurements from noninvasive pressure sensor devices) on the patient monitoring device in the exact same way as the currently used invasive pressure measurements (i.e., analog measurements from analog pressure sensor devices, or DPTs).

It should be appreciated that aspects of the invention previously described may be implemented in conjunction with the execution of instructions by processor 224 of pressure transducer simulator 202. Processor 224 may operate under the control of a program, routine, or the execution of instructions to execute methods or processes in accordance with embodiments of the invention. For example, such a program may be implemented in firmware or software (e.g. stored in memory and/or other locations) and may be implemented by processors and/or other circuitry of the pressure transducer simulator 202. Further, it should be appreciated that the terms processor, microprocessor, circuitry, controller, etc., refer to any type of logic or circuitry capable of executing logic, commands, instructions, software, firmware, functionality, etc The various illustrative logical blocks, modules, and circuits described in connection with the embodiments disclosed herein may be implemented or performed with a general purpose processor, a microcontroller, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor or any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A pressure transducer simulator configured for use with a pressure sensor device and a monitoring device, the pressure transducer simulator configured to generate a simulation of the output of an analog pressure sensing device compatible with the monitoring device, wherein the simulation is based upon a pressure signal received from a pressure sensor device, the pressure transducer simulator comprising:
    a digital potentiometer configured to generate an analog signal based upon the pressure signal, wherein the digital potentiometer is configured to transmit the analog signal to the monitoring device; and
    a processor to implement a scaling function applied to the digital potentiometer based upon the pressure signal from the pressure sensor device and a reference excitation signal from the monitoring device to ensure the analog signal transmitted to the monitoring device is approximately equivalent to the pressure signal from the pressure sensor device.

2. The pressure transducer simulator of claim 1, wherein the digital potentiometer includes an adjustable wiper that is adjustable to select the resistance of the digital potentiometer.

3. The pressure transducer simulator of claim 2, wherein the processor determines a digital wiper setting for the adjustable wiper to select the resistance of the digital potentiometer.

4. The pressure transducer simulator of claim 3, wherein the processor implements an auto-zeroing command.

5. The pressure transducer simulator of claim 4, wherein, when the auto-zeroing command is implemented, the adjustable wiper is adjusted to set the resistance of the digital potentiometer such that the analog signal produced by the digital potentiometer and transmitted to the monitoring device is approximately zero.

6. The pressure transducer simulator of claim 3, wherein the processor implements an operate command.

7. The pressure transducer simulator of claim 6, wherein, after implementation of the operate command, the digital potentiometer produces an analog signal based upon the pressure signal from the pressure sensor device and the digital wiper setting and transmits the analog signal to the monitoring device, wherein the analog signal is approximately equivalent to the pressure signal from the pressure sensor device.

8. The pressure transducer simulator of claim 3, further comprising a buffer coupled to the digital potentiometer.

9. A method for simulating a pressure sensor device as an analog pressure sensing device to generate a simulation of the output of an analog pressure sensing device compatible with a monitoring device, wherein the simulation is based upon a pressure signal received from the pressure sensor device, the method comprising:
- configuring a digital potentiometer to generate an analog signal based upon the pressure signal;
- transmitting the analog signal to the monitoring device; and
- implementing a scaling function applied to the digital potentiometer based upon the pressure signal from the pressure sensor device and a reference excitation signal from the monitoring device to ensure the analog signal transmitted to the monitoring device is approximately equivalent to the pressure signal from the pressure sensor device.

10. The method of claim 9, wherein the digital potentiometer includes an adjustable wiper that is adjustable to select the resistance of the digital potentiometer.

11. The method of claim 10, further comprising determining a digital wiper setting for the adjustable wiper to select the resistance of the digital potentiometer.

12. The method of claim 11, further comprising implementing an auto-zeroing command, wherein the adjustable wiper is adjusted to set the resistance of the digital potentiometer such that the analog signal produced by the digital potentiometer and transmitted to the monitoring device is approximately zero.

13. The method of claim 11, further comprising implementing an operate command, wherein the adjustable wiper is adjusted to set the resistance of the digital potentiometer to produce an analog signal approximately equivalent to the pressure signal from the pressure sensor device and to transmit the analog signal to the monitoring device.

14. A pressure transducer simulator configured for use with a pressure sensor device and a monitoring device, the pressure transducer simulator configured to generate a simulation of the output of an analog pressure sensing device compatible with the monitoring device, wherein the simulation is based upon a pressure signal received from the pressure sensor device, the pressure transducer simulator comprising:
- a digital potentiometer including an adjustable wiper that is adjustable to select the resistance of the digital potentiometer, wherein the digital potentiometer is configured to generate an analog signal based upon the pressure signal and a digital wiper setting and to transmit the analog signal to the monitoring device; and
- a processor to implement an auto-zeroing command and an operate command and to apply a scaling function to the digital potentiometer based upon the pressure signal from the pressure sensor device and a reference excitation signal from the monitoring device to ensure the analog signal transmitted to the monitoring device is approximately equivalent to the pressure signal from the pressure sensor device.

15. The pressure transducer simulator of claim 14, wherein the processor determines a digital wiper setting for the adjustable wiper to select the resistance of the digital potentiometer.

16. The pressure transducer simulator of claim 15, wherein, when the auto-zeroing command is implemented, the adjustable wiper is adjusted to set the resistance of the digital potentiometer such that the analog signal produced by the digital potentiometer and transmitted to the monitoring device is approximately zero.

17. The pressure transducer simulator of claim 15, wherein, after implementation of the operate command, the digital potentiometer produces an analog signal based upon the pressure signal from the pressure sensor device and the digital wiper setting and transmits the analog signal to the monitoring device, wherein the analog signal is approximately equivalent to the pressure signal from the pressure sensor device.

* * * * *